United States Patent [19]

Morales et al.

[11] Patent Number: 5,730,973
[45] Date of Patent: Mar. 24, 1998

[54] **WATER-DISPERSIBLE GRANULES OF SPORES OR LIVE *BEAUVERIA BASSIANA***

[75] Inventors: Esperanza Morales, Bogota, Colombia; Hans Röchling, Bad Soden, Germany

[73] Assignee: Hoechst Schering AgrEvo GmbH, Berlin, Germany

[21] Appl. No.: 387,274

[22] Filed: Feb. 13, 1995

[30] Foreign Application Priority Data

Feb. 15, 1994 [DE] Germany .................. 44 04 702.9

[51] Int. Cl.$^6$ ............................................. A01N 63/04
[52] U.S. Cl. .................. 424/93.5; 424/405; 424/489; 435/254.1; 435/911
[58] Field of Search ................ 424/93.5, 405, 424/489; 435/254.1, 911

[56] References Cited

U.S. PATENT DOCUMENTS

| | | | |
|---|---|---|---|
| 3,549,555 | 12/1970 | Hiestand et al. | 252/316 |
| 3,986,979 | 10/1976 | Moorer et al. | 252/353 |
| 4,233,178 | 11/1980 | Fuchigami | 252/316 |
| 4,725,436 | 2/1988 | Prilwitz et al. | 424/93 |
| 4,777,762 | 10/1988 | Redenbaugh | 47/57.6 |
| 4,865,842 | 9/1989 | Brandbury et al. | 424/93 |
| 5,084,272 | 1/1992 | Speakman et al. | 424/93 |
| 5,102,794 | 4/1992 | Taguchi et al. | 435/126 |
| 5,125,967 | 6/1992 | Morpeth et al. | 106/18.22 |
| 5,147,640 | 9/1992 | Gard et al. | 424/934 |
| 5,187,185 | 2/1993 | Outcalt et al. | 514/408 |
| 5,413,784 | 5/1995 | Wright et al. | 424/93.5 |

FOREIGN PATENT DOCUMENTS

| | | |
|---|---|---|
| 0485229 | 5/1992 | European Pat. Off. . |
| 2358105 | 2/1978 | France . |

OTHER PUBLICATIONS

Rehm et al, "Biotechnology", vol. 3 1986, pp. 30–34.

*Primary Examiner*—Irene Marx
*Attorney, Agent, or Firm*—Frommer Lawrence & Haug LLP

[57] ABSTRACT

Disclosed and claimed are granules containing: (a) 5 to 80% with weight of spores or active units of one or more organisms which act as pesticides or plant treatment agents, (b) 5 to 60% by weight of one or more suitable wetting agents and dispersants, (c) 2 to 50% by weight of at least one protective substance which prevents desiccation, (d) 5 to 70% by weight of magnesium silicate or aluminum silicate, (e) 0.5 to 20% by weight of at least one substance which protects against UV radiation, and (f) a residual water content of 2–10%. The granules are a spray formulation which can be used as pesticides or plant treatment products. The granules have storage stability and are free-flowing, low in dust and readily measured out in use.

8 Claims, No Drawings

WATER-DISPERSIBLE GRANULES OF SPORES OR LIVE *BEAUVERIA BASSIANA*

FIELD OF THE INVENTION

The present invention relates to novel crop protection products comprising live organisms, formulated as granules which are dispersible in aqueous media.

BACKGROUND OF THE INVENTION

It is known that certain microorganisms such as bacteria, viruses, fungi, and nematodes, can be pathogenic to pests and are suitable for the treatment of plants. However, determining suitable formulations containing live organisms to be used in practice can be problematic. In the formulation process, a large proportion of the microorganisms lose their viability, or, at room temperatures, lose their activity within a few days. It is therefore difficult to prepare formulations that meet the requirements for agricultural purposes.

The use of microorganisms for crop protection currently is limited since there is no formulation that guarantees stability of the microorganisms and homogeneity of the product. Formulations that provide the pulverulent product in the form of a dust or aqueous dispersion are mentioned in the literature. Other formulations include oily dispersions and granules.

The paper of Pereira and Roberts, J. Economical Entomology 84:1657–1661 (1991) relates to a pulverulent dry mycelium of entomopathogenic fungi encapsulated in alginate or corn starch. This type of preparation can be used as a granule for dissemination against soil-dwelling pests. The stability of the product varies as a function of the fungal species, the storage temperature and the type of encapsulation.

French Patent specification FR 2494717 describes crop protection products composed of robust spores of entomophthoral fungi covered by chalk. These may be used in the form of wettable or atomizable powders. The stability of the product is guaranteed for two months at a storage temperature of 2° to 7° C.

Patent Specification WO 92/20229 mentions the use of biopolymers as carriers, coatings and nutrients for microorganisms, which are employed as pesticides. No statements are made by the authors about storage stability, homogeneity or other factors such as dispersibility or suspendibility, from which conclusions might be drawn regarding the economy of the product.

French Patent Publication FR 2394606 relates to the preservation and the protection of microorganisms by means of chalk. However, the publication does not describe an end product that might be suitable for agricultural use.

U.S. Pat. No. 4,530,834 mentions the preparation of a wettable powder of dry mycelia of entomopathogenic fungi that have been treated with protective substances. The end product requires storage at 4° C.

European Patent Application EP-0 406 103 describes the growth of microorganisms on a granulated carrier that is insoluble in the fermentation medium. The particle size of the granules is between 0.5 and 2.0 mm. The end product is a spreadable granules.

European Patent EP-0 268 177 describes carrier-free cell granules of microorganisms capable of forming a mycelium. These granules are composed of microorganism cells, which grow in such a way that they form a tissue-like structure that does not contain any carrier material. These microorganisms are capable of forming cell aggregates and cell granules. They may be used for controlling pests found in the soil, on the soil or in the vicinity of the soil. The granules do not dissolve in water. The number of infectious conidia spores contained in the granules is unknown, since the conidia spores form only after application as a function of the varying microclimatic factors. Even if the optimum growth conditions were determined, there is a delay in activity due to the time required for spore formation. During this time, the granules may be eaten by animals. In this manner, some of the preparation is no longer available for spore formation.

European Patent EP-0 180 743 mentions liquid preparations of microorganisms that are covered by a protective coating and are in the form of a suspension in oil. The preparations can be stored at room temperature. These products are preferably intended for veterinary use. The authors do not refer to the homogeneity of the emulsion for agricultural purposes. U.S. application Ser. No. 892,488 by Wright and Chandler (Jun. 3, 1992); now U.S. Pat. No. 5,413,784, describes the development and assessment of a fungal preparation of *Beauveria bassiana* in oil mixed with two additional biologically active components: a synthetic pheromone and a feeding substrate, or phagostimulant. There is no information on the stability of the product as a function of storage time and storage temperature is not given.

Handling dispersions is also problematic. For example, dispersions may form sediments upon prolonged storage. Such sedimentation is difficult to disperse by shaking, and causes inhomogeneity of the product, which leads to inconsistent activity upon use. The use of wettable-powder formulations also have the disadvantage that dust is formed during use which can be a health hazard for the user.

Additionally, microorganisms are frequently deactivated, inhibited or even destroyed by surfactants, solvents, fillers, additives and other formulation auxiliaries.

OBJECTS AND SUMMARY OF THE INVENTION

It is an aim of the present invention to provide water-dispersible granule formulations containing live organisms. A further aim is formulations useful as both pesticides and plant treatment products. Another aim is formulations having storage stability at room temperature that is considerably improved in comparison with previously known, relevant formulations. Moreover, an aim is formulations which are more user friendly very easy to handle, (i.e. flowing easily), low in dust and readily measurable.

Surprisingly, it has been found that these desirable aims can be achieved by the preparation of specific, water-dispersible granules.

The granules according to the invention contain:
a) 5 to 80% by weight of spores or active units of one or more organisms, which act as pesticides or plant treatment agents,
b) 5 to 60% by weight of one or more suitable wetting agents and dispersants,
c) 2 to 50% by weight of at least one protective substance, which prevents desiccation,
d) 5 to 70% by weight of magnesium silicate or aluminum silicate,
e) 0.5 to 20% by weight of at least one substance that protects against UV irradiation, and
f) a residual water content of 2–10%.

The composition according to the invention is preferably composed as follows:

a) 20 to 50% by weight of spores or active units of one or more microorganisms, which act as pesticides or plant treatment agents, b) 10 to 40% by weight of one or more suitable wetting agents and dispersants, c) 5 to 20% by weight of vegetable oil, mineral oil, glycerol, sodium alginate or sodium glutamate as a protective substance, d) 10 to 50% by weight of magnesium silicate or aluminum silicate, e) 0.5 to 20% by weight of titanium dioxide or zinc oxide as substance that imparts UV protection, and f) a residual water content of 4–10%.

In addition to the above-mentioned ingredients, active substance formulations of the invention can contain optionally the adhesives, wetting agents, dispersants, emulsifiers, penetrants, solvents, fillers or carriers, which are customary.

DETAILED DESCRIPTION

Examples of preferred wetting agents and dispersants include sodium oleylmethyltauride (®ARKOPON T, ®HOSTAPON T), sodium methoxylignosulfonate (®VANISPESSE CB), sodium lignosulfonate (®BOSSERPERSE), a sodium dinaphthylmethanedisulfonate (®DISPERSOGEN A, ®TAMOL NNO), sodium dibutylnaphthalenesulfonate (®FERNIL DB, ®GEROPON NK), sodium polycarboxylate (®SOPROPON T36), long-chain olefin sulfonates (®HOSTAPUR OSB), isotridecanol polyglycol ether (®GENAPOL X-Marten) and polyoxyethylene sorbitan monolaurate (®TWEEN 20).

Other compounds that can be employed as protective substances are glucose, fructose, lactose or sucrose, ultrapure cellulose (®TECNOCEL consists of cellulose), and antioxidant substances such as, for example, ascorbic acid. These compounds are employed, inter alia, to prevent desiccation of the microorganisms. Thus, other compounds, which cause this effect, may also be employed as protective substances.

Preferable fillers for the preparation of the compositions according to the invention are ultra-purified magnesium silicates and aluminum silicates such as, ®BENTONE EW, ®BENTNITE 7c, finely-ground kaolins and clays, ®PERLITE, ®SANTENTONE, ®KAOLIN 1777, and Attapulgus Clay products (e.g., ®ATTACLAY, ®ATTACOTE, ®ATTAGEL, ®CLARSOL FgN-FR4 or ®KIESELGUHR).

As shown by the use of terms "one or more," "at least one," and alternative terms (e.g., "magnesium silicate or aluminum silicate"), each of ingredients a) to e) can be a mixture; for instance, ingredient b) can be a mixture of wetting agents and dispersants. The use of a combination of a plurality of protective substances, such as, for example, a mixture of glycerol, sodium alginate and sodium glutamate, is of particular interest.

Furthermore, the granules of the invention may contain silicone-based antifoams, for example antifoam ®SE2, castor-oil-based emulsifiers, such as ®EMULOGEN EL and synthetic layer silicates such as SAFONIT ®SKS20. All the formulation auxiliaries that have been mentioned are well known substances described in the specialist literature.

The term organisms within the scope of the present invention embraces single-celled and multi-celled organisms from the kingdom of the Prokaryotes and the Eukaryotes, in particular the phylum of the Schizophyta (bacteria), the phylum of the Mycophyta (fungi) and the class of the nematodes. The class of the nematodes forms part of the subphylum of the Bilateria and the tribe of the Nemathelminthes (roundworms). However, the term also embraces viruses which, being non-cellular particles, may be assigned to the organisms with some reservation.

The non-taxonomic term microorganisms is to be understood as meaning, in the context of this invention, organisms that had previously been classified under the collective name of the protists (primordial beings). It embraces organisms distinguishable by a low degree of morphological differentiation and which, are predominantly single-celled.

Microorganisms preferably employed for the preparation of the granules according to the invention are fungicidal, herbicidal, nematopathogenic and entomopathogenic microorganisms, in particular fungi from the class of the Deuteromycetes. The use of fungi of the genus Beauveria, in particular the species *Beauveria bassiana*, is of specific interest.

Furthermore, the biological formulation according to the invention offers more possibilities for the preparation of co-formulations together with other biological or chemical crop protection products, due to its chemical and physical stability. The granules according to the invention also may contain, in addition to the organisms, other pesticides (for example chemical fungicides, insecticides or herbicides) as a co-formulation.

The invention also relates to the use of the water-dispersible granules formulated according to the invention being used as crop protection products or plant treatment products, whereby upon use, the granules are diluted with water to give a spray mixture, analogous to wettable powders and liquid formulations, and applicable to the plants or the areas under cultivation in the form of a spray mixture.

The granules according to the invention are suitable particularly for controlling insects and arachnids, which are found in agriculture.

The compositions according to the invention have an outstanding insecticidal activity against a broad spectrum of economically important pests. Some representatives of pests which can be controlled by the compositions according to the invention are mentioned individually by way of example, without the enumeration being intended as a restriction to certain species.

From the order of the Isopoda, for example, *Oniscus asellus, Armadium vulgare, Porcellio scaber*. From the order of the Diplopoda, for example, *Blaniulus guttulatus*. From the order of the Chilopoda, for example, *Geophilus carpophagus, Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis, Schistocerca gregaria*. From the order of the Dermaptera, for example, *Forficula auricularia*. From the order of the Isoptera, for example, *Reculitermes spp*. From the order of the Anoplura, for example, *Phylloxera vastatrix, Pemphigus spp., Pediculus humanus corporis, Haematopinus spp., Linognathus spp.*

From the order of the Mallophaga, for example, *Trichodectes spp. and Damalinea spp*. From the order of the Thysanoptera, for example, *Hercinothrips femoralis* and *Thrips tabaci*. From the order of the Heteroptera, for example, *Eurygaster spp., Dysdercus intermedius, Piesma quadrata, Cimex lectularius, Rhodnius prolixus* and *Tri-*

*atoma* spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Scotinophora coarctata, Drasicha mangiferae, Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Heteroptera, for example, *Lygus* spp., *Nezara viridula, Drasicha mangiferae* and *Euschistus* spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Diathrea sacharalis, Bucculactrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Ostrinia* spp., *Perileucoptera coffeella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Dendrolimus* spp., *Laspeyresia pomonella.*

From the order of the Coleoptera, for example, *Anobium punctatum, Hypothemenus hampei, Pityogenes chalcographus, Cyrtomon luridus, Xyloterus lineatus, Ips typographus, Rhizopertha dominica, Bruchidius obtectus, Acenthoscelides obtectus, Hylotrupes bajulus, Agelastica alni, Leptinotarsa decemlineata, Phaeddn cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Sitona lineatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Brontispa longissima, Tenebrio molitor, Agriotes* spp., *Conoderus* spp., *Melolontha melolontha,* Sphenophorus-Levis, *Amphimallon solstitialis* and *Costelytra zealandica.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hypobosca* spp., *Glossina morsitans, Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.*

From the order of the Siphonaptera, for example, *Xenopsylla cheopis, Ceratophyllus* spp. From the order of the Arachnida, for example, *Scorpio maurus* and *Latrodectus mactans.* From the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp.

The granules according to the invention are particularly suitable for controlling sensitive and resistant *Heliothis* spp., *Anthonomus* spp., *Hypothememus hampei, Spodoptera* spp., *Nephotettix* spp., *Trichoplusia* spp., *Leptinotara decemlineata* and other feeding and sucking insects or spider mites (such as whitefly, lepidopterous larvae).

The biological crop protection products according to the invention are distinguished by a defined number of live and effective active units (for example conidia or spores) and good storage stability at room temperature, and thus have standardized activity (i.e., Consistent activity due to the ability to have in a formulation a defined number of live and effective microorganisms or spores, e.g., "Active units," and good storage stability at room temperature). Additionally, the biological crop protection products of the invention have good mechanical stability, a defined particle size, and are free-flowing, low in dust and readily measured out, which favorably affects their handling upon use.

Moreover, being water-dispersible granules, the compositions of the invention are readily wettable in water, disintegrate very rapidly and form a suspension with good suspendability characteristics.

The formulations of the prior art in contrast are disadvantageous inasfar as, to compensate for the loss caused by dissolution of the formulation in water, relatively large amounts of the substances that impart protection against UV radiation must be employed. If smaller amounts of the protective substances are employed, it must be accepted that UV protection is no longer guaranteed once the composition has been diluted in water.

In contrast, the compositions according to the invention have the advantage that optimum protection against UV can be guaranteed due to the special formulation, even after the product has been dissolved in water.

Thus, an important advantage of the compositions according to the invention is that the active live materials can be treated very specifically using smaller amounts of substances with a protective action whose activity is not reduced even when diluted highly with water. It is this fact which distinguishes this type of formulation from all other formulations of microorganisms known to date.

EXAMPLES

The examples which follow are intended to illustrate the invention without imposing any limitation. Unless otherwise specified, percentages are by weight:

Preparation examples of the formulations

A large number of processes are available for the technical preparation of water-dispersible granules: for example, they can be prepared in a rapidly rotating disc or drum granulator. Alternatively, they can be produced in a kneader-extruder or in a fluidized bed. A more detailed description of the preparation process is found, for example, in: H. B. Ries "Granuliertechnik und Granuliergeräte" [Granulation Technology and Granulation Apparatus] in Aufbereitungstechnik No. 3 (1970); M. Rosch and R. Probst in Verfahrenstechnik No. 9 (1975); U.S. Pat. No. 3,920,442; GB-A 1401304; EP-A 0026918; EP-A 0141436 and EP-A 0141437.

To prepare the water-dispersible granules, fine aluminum silicate or magnesium aluminum silicate, and/or synthetic layer silicate is first mixed with a solid wetting agent and dispersant. A range of solid substances having a protective action may also be added. The resulting powder mixture is introduced into a fluidized bed or a kneader and granulated by spraying with an aqueous fungal dispersion.

For the preparation of small amounts, a laboratory-scale fluidized bed granulation apparatus such as, for example, BÜCHI 710, or a kneader, for example SIGMA LUK manufactured by Werner & Pfleiderer, and a piston extruder, may be used.

For assessment of the granules, the dispersibility, suspendability and wet-screening residue values of the granules may be determined.

The spontaneous dispersibility of the granule formulation is assessed using a 1-to-4 key. For this purpose, 1 g of the granules are first placed into a 1 liter graduated cylinder filled with standardized water (30° C., water hardness 342 ppm of $CaCO_3$). After 1 minute, the graduated cylinder is rotated slowly by 180° and then returned to the starting position. This procedure is repeated three times. The result is assessed using the following key:

1. All granules are dispersed. If any undispersed granules are present, the shaking process described above is repeated three times 2 minutes after the beginning of the experiment, and the result is assessed as follows:
2. The granules are now fully dispersed.
3. Remains of the granules are not dispersed.
4. Most of the granules are not dispersed.

The suspendability is the amount of the preparation (% by weight) which is suspended in the upper nine-tenths parts by volume after a sedimentation time of 30 minutes has elapsed (see CIPAC Handbook Vol. 1 (1970), p. 861).

The term wet-screening residue defines the amount of substance that remains on screens of dimensions 250 μm and 71 μm, respectively, after washing for 10 minutes with a defined amount of water. The method is described in "Richtlinien für die amtliche Prüfung von Pflanzenschutzmitteln, Teil III, 2-1/1 (August 1988) der Biologischen Bundesanstalt Braunschweig" [Guidelines for the official testing of crop protection products, Part III, 2-1/1 (August 1988) of the Federal Institute of Biology].

Example 1

Extruder WG of *Beauveria bassiana*

A. Preparation of an aqueous dispersion of Beauveria:

| | % by weight |
|---|---|
| Fungal spores | 25.0 |
| GENAPOL X-060 | 2.5 |
| Glycerol | 1.5 |
| Sodium glutamate (protective substances) | 0.5 |
| Sodium alginate | 0.5 |
| Water | 70.0 |
| | 100.0 |

The components are mixed by stirring until a fine, highly-concentrated, homogeneous dispersion has formed.

B. The resulting dispersion is sprayed onto a powder mixture while being kneaded continuously. The ratio by weight of dispersion to powder mixture is 8:7.

The powder mixture used has the following composition:

| | % by weight |
|---|---|
| Sucrose | 7.1 |
| BENTONE EW | 2.8 |
| BENTONITE 7C | 28.5 |
| TECNOCEL | 11.5 |
| KIESELGUHR | 28.5 |
| SAPONIT SKS 2C | 1.5 |
| VANISPERSE CB | 11.5 |
| GEROPON NK | 2.8 |
| HOSTAPON T | 5.8 |
| | 100.0 |

C. Using the resulting paste, the granules are prepared and dried in a fluidized bed dryer at a product temperature of 30° C. until the residual moisture content is 6%.

The final composition of the water-dispersible granules is:

| | % by weight |
|---|---|
| Fungal spores | 20.0 |
| GENAPOL X 060 | 2.0 |
| Glycerol | 1.2 |
| Sodium glutamate | 0.4 |
| Sodium alginate | 0.4 |
| Sucrose | 5.0 |
| BENTONE EW | 2.0 |
| BENTONITE 7C | 20.0 |
| KIESELGUHR | 20.0 |
| TECNOCEL | 8.0 |
| VANISPERSE CB | 8.0 |
| GEROPON NK | 2.0 |
| HOSTAPON T | 4.0 |
| SAPONITE SKS 2CV | 1.0 |
| Water | 6.0 |
| | 100.0 |

Using a key from 1 to 4, the spontaneous dispersibility is 2 (dispersing time 5 minutes). The suspendability is 87%. Using a 71 μm screen, the wet-screening residue is 0.7%; if a 250 μm screen is used, no residue is found.

Example 2

Fluidized bed WDG of *Beauveria bassiana*

A. Preparation of the aqueous Beauveria dispersion:

| | % by weight |
|---|---|
| Fungal spores | 10.0 |
| GENAPOL X-060 | 1.0 |
| Glycerol | 0.6 |
| Sodium glutamate | 0.2 |
| Sodium alginate | 0.2 |
| Sucrose | 2.5 |
| Water | 85.5 |
| | 100.0 |

The components are stirred until a fine homogeneous dispersion has formed.

B. A powder mixture is introduced into a fluidized bed, and the dispersion is sprayed onto this powder mixture at a product temperature of 30° C., and the product is subsequently dried. The ratio by weight of dispersion to powder mixture is 20:6.5.

The powder mixture has the following composition:

| | % by weight |
|---|---|
| CLARSOL GFN-FR4 | 30.5 |
| KAOLIN 1777 | 23.5 |
| KIESELGUHR | 23.5 |
| VANISPERSE CB | 12.0 |
| GEROPON NK | 3.0 |
| HOSTAPON T | 6.0 |
| SAPONIT SKS 20 | 1.5 |
| | 100.0 |

C. The final composition of the water-dispersible granules is as follows:

| | % by weight |
|---|---|
| Fungal spores | 20.0 |
| GENAPOL X-060 | 2.0 |
| Glycerol | 1.2 |
| Sodium glutamate | 0.4 |
| Sodium alginate | 0.4 |
| Sucrose | 5.0 |
| CLARSOL FGN-FR4 | 20.0 |
| KAOLIN 1777 | 15.0 |
| KIESELGUHR | 15.0 |
| VANISPERSE CB | 8.0 |
| GEROPON NK | 2.0 |
| HOSTAPON T | 4.0 |
| SAPONIT SKS 20 | 1.0 |
| Water | 6.0 |
| | 100.0 |

Using a key from 1 to 4, the spontaneous dispersibility of these granules is 1. The suspendability is 97%. Using a 71 μm screen, the wet-screening residue is 0.3%; if a 250 μm screen is used, no residue is observed.

Example 3

Oil-coated Beauveria spores in extruder WDG

A. Preparation of the suspoemulsion

| | % by weight |
|---|---|
| Spores | 25.0 |
| GENAPOL X-060 | 2.5 |
| Oil | 3.7 |
| EMULSOGEN EL-400 | 0.4 |
| Water | 68.4 |
| | 100.0 |

B. A powder mixture is introduced into the kneader and sprayed with this highly concentrated suspoemulsion in a ratio by weight of 8:6.9.

The powder mixture has the following composition:

| | % by weight |
|---|---|
| BENTONE EW | 7.1 |
| BENTONITE | 28.5 |
| KIESELGUHR | 28.5 |
| TECNOCEL | 14.3 |
| VANISPERSE CB | 11.5 |
| GEROPON NK | 2.8 |

-continued

| | % by weight |
|---|---|
| HOSTAPON T | 5.8 |
| SAPONIT SKS 20 | 1.5 |
| | 100.0 |

The granules are produced in an extruder and dried in a fluidized bed dryer at a product temperature of 30° C.

C. Final composition of the WDG

| | % by weight |
|---|---|
| Spores | 20.0 |
| GENAPOL X-060 | 2.0 |
| Oil | 3.0 |
| EMULSOGEN EL-400 | 0.3 |
| BENTONE EW | 3.7 |
| BENTONITE | 20.0 |
| KIESELGUHR | 20.0 |
| TECNOCEL | 10.0 |
| VANISPERSE CB | 8.0 |
| GEROPON NK | 2.0 |
| HOSTAPON T | 4.0 |
| SAPONIT SKS 20 | 1.0 |
| Water | 6.0 |
| | 100.0 |

The spontaneous dispersibility is 2. The suspendability is 89%. If using 71 μm/250 μm screens, the wet-screening residue is 0.4/0 respectively.

Example 4

UV protection of Beauveria bassiana spores in extruder WDG by means of $TiO_2$

A. Preparation of the supoemulsion:

| | % by weight |
|---|---|
| Fungal spores | 20.0 |
| GENAPOL X-060 | 2.5 |
| Oil (corn oil) | 5.0 |
| EMULSOGEN EL-400 | 0.5 |
| $TiO_2$ | 0.5 |
| Water | 66.5 |
| | 100.0 |

B. A powder mixture is introduced into the kneader and sprayed with this suspoemulsion in a ratio by weight between dispersion and powder mixture of 8:6.7.

The composition of the powder mixture is the same as in the case of the oil-coated spores (Example 3). The final composition of the WDG is:

| | % by weight |
|---|---|
| Fungal spores | 20.0 |
| GENAPOL X-060 | 2.0 |
| Oil | 5.0 |
| EMULSOGEN EL-9.5 | 0.5 |
| $TiO_2$ | 0.5 |
| BENTONE EW | 3.0 |
| Aluminum silicates | 40.0 |
| Cellulose | 8.0 |
| VANISPERSE CB | 8.0 |
| GEROPON NK | 2.0 |

-continued

|  | % by weight |
|---|---|
| HOSTAPON T | 4.0 |
| SAPONIT | 1.0 |
| Water | 6.0 |
|  | 100.0 |

The spontaneous dispersibility is 2. The suspendability is 90%. If using 71 μm/250 μm screens, the wet-screening residue is 0.4/0. respectively.

Example 5

UV protection of *Beauveria bassiana* spores in fluidized bed WDG by means of $TiO_2$ and ZnO.

A. Preparation of the suspoemulsion:

|  | % by weight |
|---|---|
| Fungal spores | 10.00 |
| GENAPOL X-060 | 1.75 |
| Oil (groundnut oil) | 5.00 |
| EMULSOGEN EL-9.5 | 2.50 |
| $TiO_2$ | 0.25 |
| ZnO | 0.25 |
|  | 0.25 |

The components are stirred until a fine homogenous dispersion has formed.

B. A powder mixture is introduced into a fluidized bed, sprayed with the dispersion at a product temperature of 30° C. and dried. The ratio by weight of dispersion to powder mixture is 20:7. The final composition of the water-dispersible granules is:

|  | % by weight |
|---|---|
| Fungal spores | 20.0 |
| Genapol X-060 | 3.5 |
| Oil (groundnut oil) | 5.0 |
| Emulsogen EL-9.5 | 0.5 |
| $TiO_2$ | 0.5 |
| ZnO | 0.5 |
| CLARSOL FGN-FR4 | 20.0 |
| KAOLIN 1777 | 15.0 |
| KIESELGUHR | 10.0 |
| BENTONE EW | 5.0 |
| SAPONIT SKS 20 | 1.0 |
| VANISPERSE CB | 8.0 |
| GEROPON NK | 2.0 |
| HOSTAPON T | 3.0 |
| Water | 6.0 |
|  | 100.0 |

The spontaneous dispersibility of these granules is 1, the suspendability is 95%, and the wet-screening residue is 0.3%/0 if using 71/250 μm screens, respectively.

I claim:

1. Water-dispersible granules which consist essentially of
a) 1 to 80% by weight of live entomopathogenic *Beauveria bassiana* or spores thereof,
b) 5 to 60% by weight of at least one wetting agent, or at least one dispersant, or at least one wetting agent and at least one disperant, selected from the group consisting of sodium oleylmethyltauride, sodium methoxylignosulfonate, sodium lignosulfonate, a sodium dinaphthylmethanedisulfonate, sodium dibutylnaphthalenesulfonate, sodium polycarboxylate, long-chain olefin sulfonates, isotridecanol polyglycol ether and polyoxyethylene sorbitan monolaurate,
c) 2 to 50% by weight of at least one protective substance which prevents desiccation, selected from the group consisting of vegetable oil, mineral oil, glycerol, sodium alginate, sodium glutamate, glucose, fructose, lactose, sucrose, and cellulose,
d) 5 to 70% by weight of magnesium silicate or aluminum silicate, and
e) 0.5 to 20% by weight of at least one substance which protects against UV radiation, selected from the group consisting of titanium dioxide and zinc oxide, and
f) a residual water content of 2–10%.

2. The water-dispersible granules as claimed in claim 1, which consist essentially of
a) 20 to 50% by weight of live entomopathogenic *Beauveria bassiana* or spores thereof,
b) 10 to 40% by weight of the at least one wetting agent, or at least one dispersant, or at least One wetting agent and at least one dispersant,
c) 5 to 20% by weight of the protective substance which prevents desiccation,
d) 10 to 50% by weight of magnesium silicate or aluminum silicate,
e) 0.5 to 20% by weight of titanium dioxide or zinc oxide, and
f) a residual water content of 4–10%.

3. The granules as claimed in claim 1, wherein the 1 to 80% by weight of the live entomopathogenic *Beauveria bassiana* or spores thereof is the live entomopathogenic *Beauveria bassiana*.

4. A method of controlling arachnids comprising the steps of a) dispersing the granules as claimed in claim 1 in water to form a dispersion, and b) applying the dispersion to plants.

5. A method of controlling insects comprising the steps of a) dispersing the granules as claimed in claim 1 in water to form a dispersion and b) applying the dispersion to plants.

6. The granules as claimed in claim 2, wherein the 20 to 50% by weight of the live entomopathogenic *Beauveria bassiana* or spores thereof is the live entomopathogenic *Beauveria bassiana*.

7. A method of controlling arachnids comprising the steps of a) dispersing the granules as claimed in claim 2 in water to form a dispersion, and b) applying the dispersion to plants.

8. A method of controlling insects comprising the steps of a) dispersing the granules as claimed in claim 2 in water to form a dispersion, and b) applying the dispersion to plants.

* * * * *